United States Patent [19]

Knoche

[11] 4,317,241

[45] * Mar. 2, 1982

[54] BREAST PROSTHESIS

[76] Inventor: Bodo Knoche, Stöckumer Str. 24, D-3204 Nordstemmen 4, Fed. Rep. of Germany

[*] Notice: The portion of the term of this patent subsequent to Apr. 29, 1997, has been disclaimed.

[21] Appl. No.: 145,706

[22] Filed: May 1, 1980

[51] Int. Cl.³ .............................................. A61F 1/00
[52] U.S. Cl. .......................................... 3/36; 264/222; 264/DIG. 30
[58] Field of Search ............. 3/36; 264/222, DIG. 30; 249/55

[56] References Cited

U.S. PATENT DOCUMENTS 4,086,666  5/1978  Vaskys et al. ............................. 3/36
4,199,825  4/1980  Knoche ..................................... 3/36

FOREIGN PATENT DOCUMENTS 2605148  8/1977  Fed. Rep. of Germany ............ 3/36

*Primary Examiner*—Clifford D. Crowder
*Attorney, Agent, or Firm*—Toren, McGeady & Stanger

[57] ABSTRACT

A breast prosthesis for use as a replacement in the case of a mastectomy where the chest of the wearer presents problems in providing a satisfactory support surface for a standardized prosthesis. The prosthesis includes an internal filler part which seats in the cavity so that the prosthesis assumes its normal position.

3 Claims, 7 Drawing Figures

BREAST PROSTHESIS

SUMMARY OF THE INVENTION

The present invention is directed to a breast prosthesis such as is used as a replacement in the case of a mastectomy and, more particularly, to a prosthesis where the chest of the wearer presents problems in providing a satisfactory support surface for a standarized prosthesis.

In co-pending patent application Ser. No. 841,478, filed Oct. 12, 1977 by Bodo Knoche, now U.S. Pat. No. 4,199,825, a breast prosthesis and a method of molding the prosthesis have been disclosed. This breast prosthesis has met with considerable success, however, it has been noted in certain instances that the prosthesis does not fit properly because of the cicatrization formed following a mastectomy. Usually the chest of a person who has undergone a mastectomy follows the normal chest curvature, but without the amputated breast. When a standardized prosthesis formed in accordance with regular brassiere cup sizes, is placed on such a normal chest surface it fits properly. In certain instances, however, because of the nature of the operation performed and the amount of tissue and muscle removed, after the healing process, a cavity or depression is present inwardly from the normal chest surface.

The breast prosthesis formed in accordance with the above mentioned patent is intended to be used where the chest surface of the wearer is smooth and follows the normal chest curvature without any cavity or depression. If there is a cavity or depression inwardly of the normal chest surface, when the prosthesis is placed on the wearer it tends to sink in and does not fit properly in the brassiere cup for which it is designed.

A breast prosthesis, such as in the above-mentioned Knoche patent, is designed to conform with the shape and appearance of a wearer's natural breast when wearing a brassiere. If, because of a cavity in the wearer's chest, the breast prosthesis sized to the wearer's natural breast does not fit properly, the use of a larger prosthesis in an attempt to overcome the presence of the cavity results in a poor fit in the brassiere normally worn by the wearer and there is no balance or symmetry with the remaining natural breast. To assure proper balance the prosthesis must conform in size and appearance to the natural breast.

Therefore, it is the primary object of the present invention to provide a prosthesis which overcomes the problems present where the chest surface, on which the prosthesis rests, includes a cavity or other uneven condition preventing the use of a standardized prosthesis.

In accordance with the present invention, a standardized prosthesis is molded with additional parts which seat in the cavity and provide an adequate support for the breast prosthesis which conforms to the natural breast of the wearer.

Once it has been determined that a standardized prosthesis does not fit properly on the wearer's chest because of some cavity or the like, it is necessary to take an impression of the chest of the wearer to provide a part which, when molded with a standardized prosthesis will fill at least in part the cavity so that the prosthesis can be set in place without any imbalance with the natural breast.

After an impression of the chest cavity is made, the impression along with the proper prosthesis are used to make a mold, and with the mold a prosthesis is formed which includes the material required to fill the cavity or at least provide a satisfactory base for the prosthesis so that, when worn with a brassiere, it provides proper balance and symmetry with the wearer's natural breast.

The present invention also includes the provision of a prosthesis for a part of a breast when only a portion of a breast is removed in a mastectomy or when, for some other reason, it is deformed and includes a cavity.

In forming such a prosthesis, an impression material is filled into the cavity present because of the missing part of the breast. The outer surface of the impression material is shaped to the normal breast line and then removed. The impression material is used to form a mold and, using the mold, a prosthesis is produced to place in the cavity so that, when worn in a brassiere the prosthesis gives the appearance of the wearer's natural breast.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described embodiments of the invention.

DETAIL DESCRIPTION OF THE INVENTION

Figure 1:
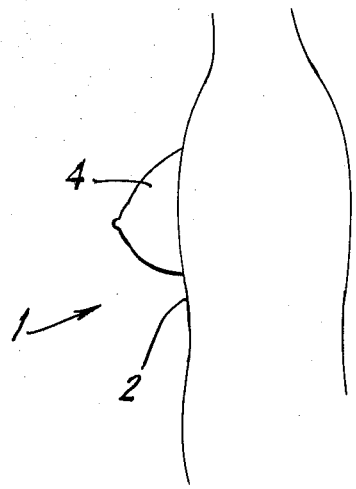
FIG. 1 is a schematic side view of the normal chest surface of a person who has undergone a mastectomy.

In FIG. 1 the chest case of a woman who has undergone a mastectomy is represented by 1 with the line 2 representing the normal chest surface after the mastectomy. A breast prosthesis 4, such as disclosed in the above-mentioned patent to Knoche, is placed over the site of the amputated breast. The prosthesis 4 is sized to conform to the shape and appearance of the wearer's natural breast when worn with a brassiere.

Figure 2:
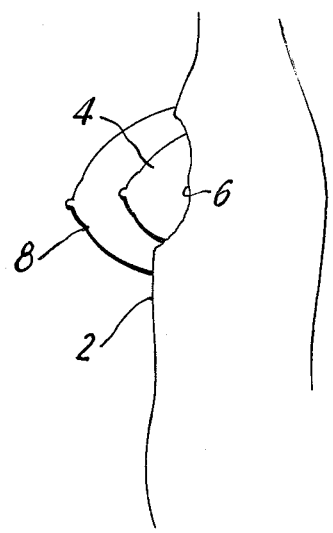
FIG. 2 is a schematic side view of the chest surface of a person who has undergone a mastectomy with a cavity formed inwardly of the normal chest surface.

In FIG. 2, because of the removal of more tissue or muscle than is usual, after the mastectomy operation has healed, a cavity 6 remains formed inwardly of the line 2 of the normal chest surface. The overall dimensions of the cavity in the vertical and horizontal directions as well as its depth inwardly of the normal line 2 of the chest case can vary very significantly.

In FIG. 2, the breast prosthesis 4 which would normally conform to the natural breast of the wearer when placed over the site of the amputated breast fits inwardly from the normal position and, because of the irregular cavity surface, may not be oriented in the manner of a natural breast. If a larger standardized prosthesis 8 is used to overcome the effects of a cavity 6, an imbalance will result with the remaining natural breast of the wearer. Since the prosthesis is intended to be worn with a brassiere the wearer would be unable to use the size intended for her natural breast and the result would be not only an imbalance between the natural and the artificial breast but also a poor fit of the brassiere. The effect of such a result can cause the wearer great mental distress.

To be able to use the standardized prosthesis which corresponds to the wearer's natural breast, initially an impression material 10 is filled into the cavity 6 in the chest of the wearer so that the configuration of the chest case 1 over the filled-in cavity 6 conforms to the normal line 2 of the chest. Any normal impression material can be used which is capable of use in the making of a mold, the breast prosthesis corresponding to the wearer's natural breast is placed over the filled-in cavity 6 in the proper location. To assure the proper positioning of the prosthesis the wearer puts on her regular brassiere so that the location of the prosthesis 4 relative to the impression 10 in the filled-in cavity 6 can be determined. The relative positions of the prosthesis and the impression are established by placing index marks 7 on both, note FIG. 3a.

Figure 3:
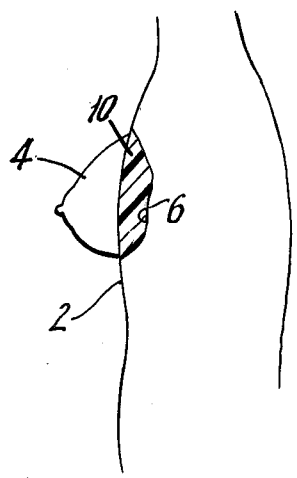
FIG. 3 is a schematic side view similar to FIG. 2 showing the cavity filled with an impression material.
Figure 3A:
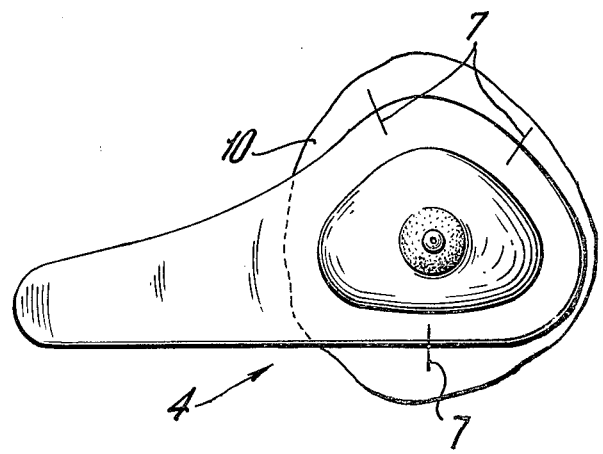
FIG. 3a is a front view of a standardized prosthesis indexed over impression material in the cavity in the chest case of the wearer.

With the prosthesis 4 properly positioned and indexed relative to the filled-in cavity 6, the prosthesis and the impression are removed from the wearer. Using the prosthesis 4 and the impression material 10, as shown in FIG. 3, the two parts are arranged one relative to the other in accordance with the index marks 7 of FIG. 3a previously established and using this combination of the prosthesis and impression material a mold is formed.

After making the mold a prosthesis is formed incorporating the material required to fill the cavity in the chest of the wearer. The above-mentioned Knoche patent is incorporated herein by reference for indicating the manner of forming the prosthesis and the materials used in making it.

Figure 4:
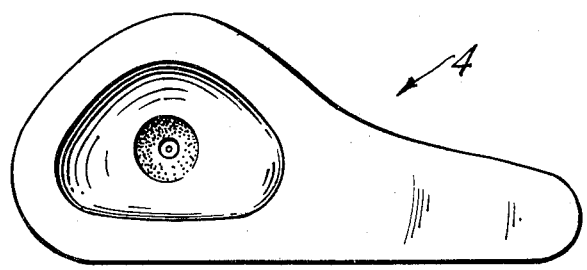
FIG. 4 is a rear view of a standardized breast prosthesis.
Figure 5:
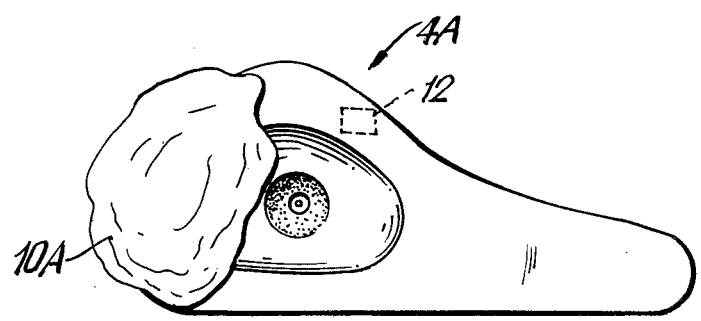
FIG. 5 is a rear view of a breast prosthesis including an integral part for filling a cavity shown in FIG. 2.

In FIG. 4 a prosthesis 4 as formed in accordance with the Knoche patent, mentioned above, is shown from the rear, that is, the side of the prosthesis which is placed against the chest of the wearer. The interior of the prosthesis is hollowed out as explained in the patent. When the combination of the prosthesis 4 and the impression material 10 conforming to the cavity is molded the hollow interior of the prosthesis remains with the part corresponding to the impression material 10 projecting from the rear surface of the prosthesis. The molded prosthesis 4A is shown in FIG. 5 and corresponds to the standardized prosthesis 4 for that portion which extends outwardly from the normal chest line 2 of the wearer, however, the additional filler part 10A formed integrally with its rear surface fits into the cavity of the chest of the wearer and assures that there is a proper balance with the wearer's natural breast. The disclosure of the Knoche patent sets forth the structure of and the materials and procedures used in forming the standardized prosthesis 4 and is incorporated herein by reference. The same structure materials and procedures would be used for forming the prosthesis embodying the present invention, however, a special mold is needed to provide the filler part 10A corresponding to the impression.

To assure that the prosthesis is properly positioned and held in place on the wearer's chest, a recess 12 can be formed in the edge portion of the prosthesis, note the dotted lines shown in FIG. 5, in which an insert of Velcro can be placed. A similar piece of Velcro can be adhered to the chest of the wearer so that the two pieces interengage when the breast prosthesis is positioned on the wearer's chest to assure that it is held in place and does not move out of position.

Figure 6:
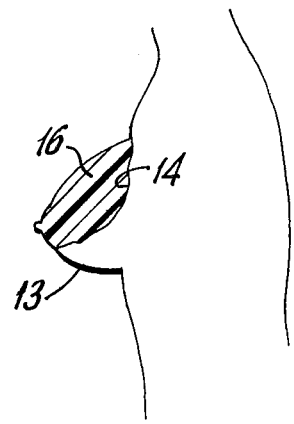
FIG. 6 is a schematic side view of a person who has undergone a partial mastectomy or who has a deformed breast where a cavity is formed in the breast.

In FIG. 6 a breast 12 is shown of a person on whom a partial mastectomy has been performed or whose breast is deformed for some other reason and includes a recessed portion 14 extending inwardly from the normal breast line. To provide a prosthesis 16, shown hatched, so that when worn inside a brassiere it gives the appearance of a natural breast, an impression material is filled into the cavity or recessed portion 14. The outer surface of the impression material is shaped to conform to the natural breast line of the person. The impression material is removed and used to form a mold. Using the mold a prosthesis is produced representing only a portion of a breast. When this prosthesis is placed in the recess in the person's breast and worn in a brassiere it give a completely natural appearance. If necessary, means can be provided for holding the prosthesis in place.

While specific embodiments of the invention have been shown and described in detail to illustrate the application of the inventive principles, it will be understood that the invention may be embodied otherwise without departing from such principles.

What is claimed is:

1. A breast prosthesis die cast formed of a skin-colored soft silicone rubber cross-linked with an amount of hardeners such that it vulcanizes to a soft elastic material forming an outer surface facing outwardly away from a wearer and an inner surface facing inwardly toward the wearer, and comprising an integral base including a central part, an edge extension and a flap-like section, said central part having a convex outer surface and a concave inner surface forming a hollow cup-shaped form, said convex outer surface having the shape of a female breast including a nipple and an areola, said concave inner surface having a breast-like shape being spaced from the outer surface and forming therebetween the wall thickness of the central part, said central part having a passage extending through said nipple from the outer surface to the inner surface, said edge extensions being thin and flexible and laterally enclosing said central part, said edge extension having a width outwardly from said central part so that said edge extension does not extend outwardly from the edge of a brassiere with which it is worn, said flap-like section connected to said edge extension and extending laterally outwardly from said central part toward the closest side of the wearer with said flap-like section having a length and width sufficient for covering the auxillary lymph-gland area when the prosthesis is in place, wherein the improvement comprises a filler part formed integrally with said inner surface of said prosthesis and being attached to said edge extension, said filler part projecting from said edge extension away from the hollow cup-shaped form of said central part so that said filler part fits into a cavity formed inwardly of the normal line of the chest case of the wearer whereby the prosthesis assumes its normal position.

2. A method of forming a breast prosthesis for use by a person having a cavity formed inwardly from the normal chest line after a breast has been amputated in a mastectomy operation, comprising the steps of filling the cavity area with an impression material so that the outer surface of the material conforms to the normal chest line of the wearer, positioning a prosthesis over the impression material, indexing the position of the prosthesis and the impression material relative to one another, removing the impression material and the prosthesis, positioning the removed prosthesis and impression material relative to one another and utilizing the prosthesis and impression material for forming a mold, and using the mold forming a combined prosthesis and filler part so that the filler part seats into the cavity and locates the prosthesis in the proper position.

3. Method, as set forth in claim 2, wherein after placing the prosthesis over the impression material in the cavity of the wearer's chest, putting a brassiere of the normal size worn by the wearer over the prosthesis and filler material for locating the prosthesis relative to the impression material, placing indexing marks on the prosthesis and the filler material so that after the prosthesis and filler material are removed individually they can be combined utilizing the index marks into the correct relative position for forming the mold.

* * * * *